(12) United States Patent
Martti et al.

(10) Patent No.: US 7,029,176 B2
(45) Date of Patent: Apr. 18, 2006

(54) X-RAY APPARATUS FOR INTRAORAL IMAGING APPLICATIONS

(75) Inventors: Juhani Martti, Helsinki (FI); Pekka Ihalainen, Helsinki (FI)

(73) Assignee: Instrumentarium Corp., Tuusula (FI)

( * ) Notice: Subject to any disclaimer, the term of this patent is extended or adjusted under 35 U.S.C. 154(b) by 7 days.

(21) Appl. No.: 10/662,047

(22) Filed: Sep. 12, 2003

(65) Prior Publication Data

US 2005/0058258 A1 Mar. 17, 2005

(51) Int. Cl.
*H05G 1/02* (2006.01)

(52) U.S. Cl. .................................................. 378/197
(58) Field of Classification Search .............. 378/38, 378/39, 40, 168, 193, 197
See application file for complete search history.

(56) References Cited

U.S. PATENT DOCUMENTS

| | | | | |
|---|---|---|---|---|
| D290,500 S | * | 6/1987 | Makas et al. | D24/158 |
| 4,893,321 A | * | 1/1990 | Eitner et al. | 378/121 |
| 6,434,329 B1 | * | 8/2002 | Dube et al. | 396/14 |
| 6,898,268 B1 | | 5/2005 | Makila et al. | 378/38 |

* cited by examiner

*Primary Examiner*—Edward J. Glick
*Assistant Examiner*—Courtney Thomas
(74) *Attorney, Agent, or Firm*—Andrus, Sceales, Starke & Sawall, LLP

(57) ABSTRACT

An x-ray apparatus for intraoral imaging applications includes a linkage mounted on a support structure, to which is connected an x-ray source for generating x-radiation and directing same to a receiver instrument placed in a patient's mouth. The linkage includes a first arm member, articulated to the support structure and adapted to be pivotable about a substantially vertical axis, a second arm member, connected to the end of the first arm member spaced from the support structure and adapted to be pivotable around a substantially vertical axis and a horizontal axis, and a third arm member, connected to the opposite end of the second arm member and adapted to be pivotable around a substantially horizontal axis, the unsupported end of the latter having the x-ray source mounted thereon with an articulated joint, which allows pivoting of the x-ray source to various positions.

4 Claims, 6 Drawing Sheets

X-RAY APPARATUS FOR INTRAORAL IMAGING APPLICATIONS

In dentistry, taking X-ray images of the teeth and jawbone structure is important for a reliable and successful examination of the teeth and jawbone structure. Intraoral applications are performed by using an intraorally placed X-ray detector for the reception of X-radiation. The X-radiation is emitted from an X-ray source outside the mouth to a point in the teeth and jaw structure to be examined.

PRIOR ART

The X-ray detector is typically placed in the mouth by using special retainers. The object to be imaged is irradiated with X-radiation, which is produced by an extraoral X-ray source. The X-radiation that has passed through the object is received by an X-ray detector. Positioning of the X-ray detector in the mouth and alignment of X-radiation can be varied for imaging various parts of the teeth and jaw structure.

FIG. 6 illustrates one X-ray arrangement for use in intraoral application, which is described in the present assignee's earlier U.S. Pat. No. 6,898,268. The arrangement comprises an X-ray source 100 for producing X-radiation, an X-ray detector 102 for receiving X-radiation passed through an object, and a data transfer link 104 between the X-ray source and the X-ray detector. The X-ray source 100 comprises an X-ray tube and typically also a collimator. The X-ray source is preferably carried by a linkage 106, whereby the X-ray source can be set in various radiating positions.

The X-ray detector is preferably a digital image sensor, which is divided into various imaging zones or pixels. The detector can be based e.g. on CCD (charge coupled device) technology, and it may have a dynamic area of 4096 shades of grey. The active image area has a size of 34 mm*26 mm and a resolution of 872*664 pixels. After exposure, each pixel contains an integer which is proportional to the amount of X-radiation falling on the pixel area. Optional detectors include any digital intraoral sensor, a digitized X-ray film, or any intraoral sensor device capable of converting detected X-ray photons to a digital image. It is also conceivable to use conventional x-ray detection techniques using photosensitive film to register an image, whereby a film cartridge is placed in the patient's mouth as an x-ray detector.

The X-radiation passed through an object and received by an X-ray detector is used for compiling image information. The X-ray arrangement comprises processing instruments 108 for processing the image information. The processing instruments are implemented by means of processor electronics or some other prior art electronics The processor instruments 108 are housed in their container 107 along the data transfer link 104 between the X-ray detector 102 and the X-ray source 100. It is also conceivable that the processing instruments be placed in the X-ray detector or the X-ray source. This X-ray arrangement may have connected thereto a computer unit 110 by way of the data transfer link 104. It is possible to establish a data communication from the computer unit to the processing instruments 108, the X-ray detector 102, and/or to the X-ray source 100. The processing instruments can also be housed in the computer unit. The data transfer links 104 are wired or wireless. A wired data transfer link is set up by means of a prior known cable solution. A wireless data transfer link is implemented by means of prior known transceiver solutions. In preferred embodiments, the X-ray arrangement and the data transfer link are established by means of digital technology.

At the start of imaging, the linkage 106 moves the X-ray source 100 to a correct position. Irradiation is started by pressing an exposure button 112.

The X-ray source 100 irradiates an object, e.g. a patients tooth. X-radiation is detected by the detector 102. Image information, obtained by the detection of X-radiation, is transmitted by way of the communication link 104 to the computer 110. The computer contains software for processing the image information. There may be more than one computer, and the software can be housed in more than one computer. The first computer can be e.g. a computer used for X-ray imaging and the second computer can be used for processing image information. For the sake of simplicity, just one computer 110 is shown in FIG. 6.

One problem in such a prior art X-ray arrangement for intraoral applications relates to varying space arrangements in facilities where the apparatus is to be used, whereby the linkage supporting the X-ray source must be dimensioned for a particular site, making it necessary for the linkage to have arms of various lengths. The linkage typically includes a first arm member, articulated to a support structure and adapted to be pivotable around a substantially vertical axle, a second arm member, connected to the end of the first arm member away from the support structure and adapted to be pivotable around a substantially vertical axis, and a third arm member, connected to the opposite end of the second arm member and adapted to be pivotable around a substantially horizontal axis. In terms of designing the linkage, the second and third arm members can be usually constructed from standard length arm members, the first arm member being selected from certain standard lengths according to a site of application. If the application site changes or the apparatus is relocated to necessitate an alteration of the linkage design, the first arm member is usually replaced with a new one, while the second and third arm members remain as before, because the length of the second and third arm members does not affect a minimum operating range. Such ordering and replacement of a new arm member incurs extra costs for the operator. In addition, there will be costs for the manufacturer caused by manufacturing and stocking arm members of various lengths.

SUMMARY OF THE INVENTION

Consequently, it is an object of the present invention to provide an X-ray apparatus for intraoral imaging applications, enabling a linkage to be redesigned in a relative simple manner, while providing savings in total costs. In order to fulfill this object, the inventive X-ray apparatus is provided with a length-adjustable first arm member. This length-adjustable first arm member comprises preferably two telescopically fitted, substantially rectangular profiles, the inner profile thereof having its two opposite outside surfaces formed with recesses lengthwise of the profile, with T-slots provided on the bottom thereof, and the outer profile having its inside surface formed with inward protrusions complementary to said recesses and provided with fastening through-holes for the passage of fastening elements from the outer profile's outside surface to the T-slot for locking said profiles in a desired relative position in the longitudinal direction thereof. The outer profile has its outside surface preferably provided with a lengthwise recess complementary to that in the inner profile's outside surface, and said outside-surface recesses of the outer and inner profile are provided with a cover element for making the outside surface thereof substantially flat. The fastening elements have their distal ends retained in said outside-surface recess of the outer profile and concealed under the cover element.

DESCRIPTION OF THE BEST-PREFERRED EMBODIMENT

Figure 1:
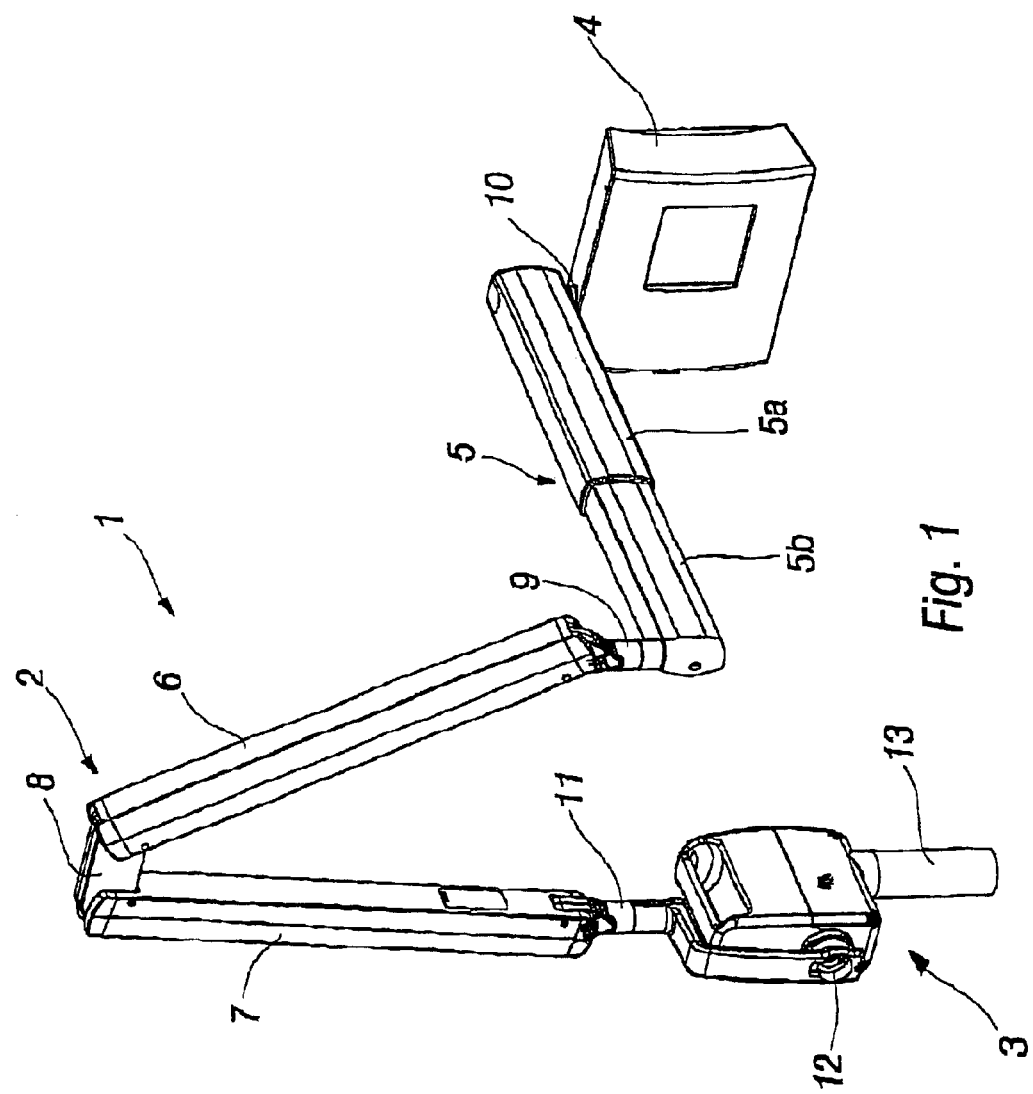
FIG. 1 shows in a schematic perspective view one exemplary embodiment for an X-ray apparatus of the invention.
Figure 2:
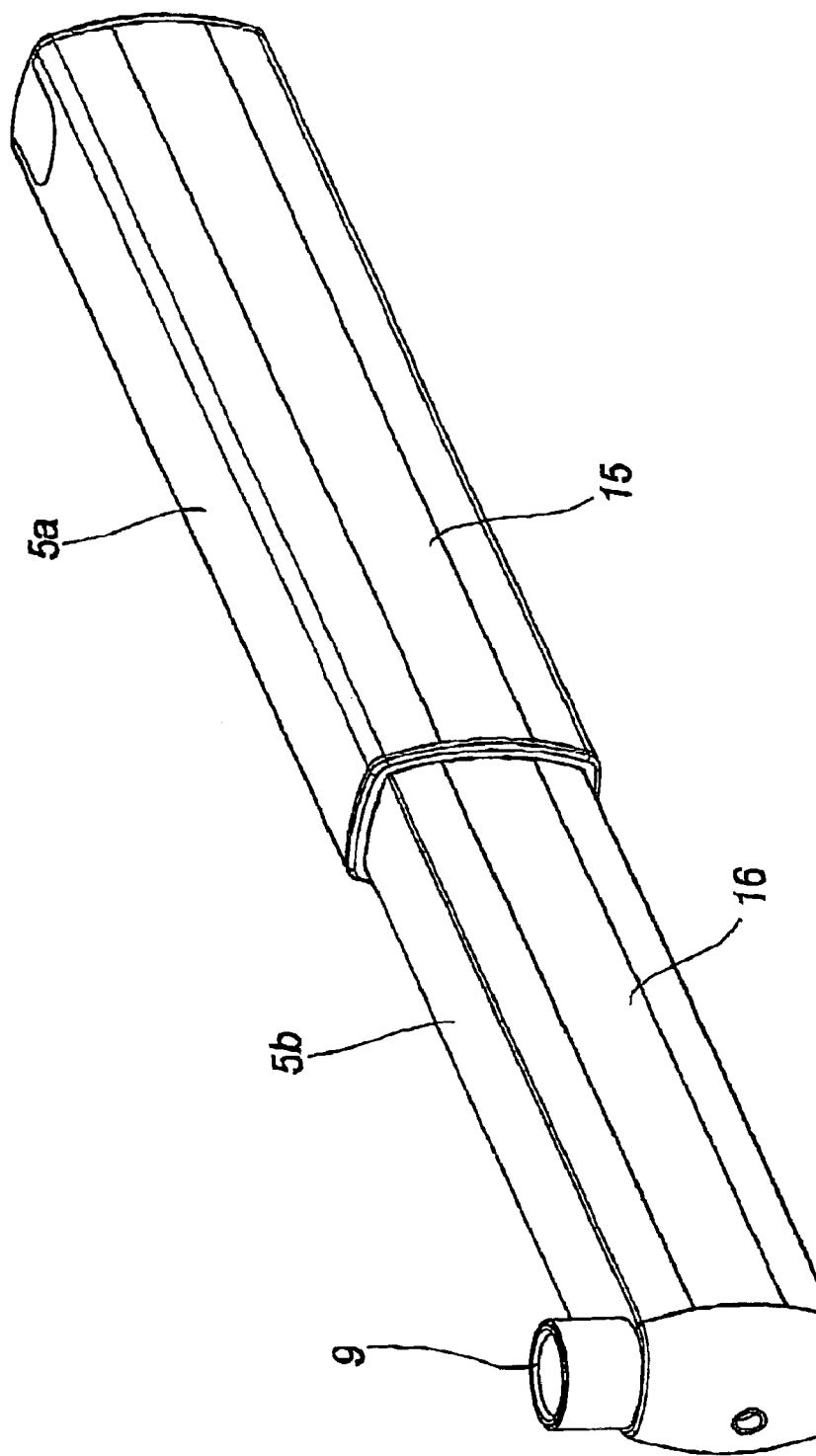
FIG. 2 shows a first arm member of the embodiment of FIG. 1, in a larger scale.
Figure 3:
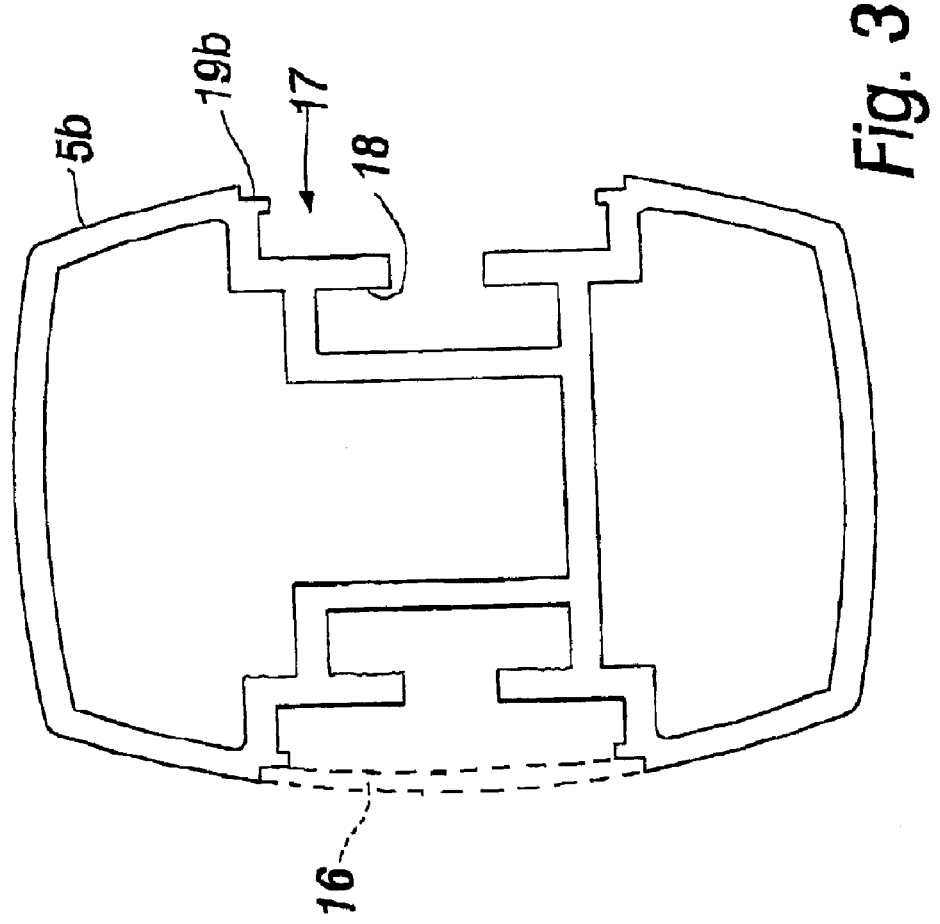
FIG. 3 shows an inner profile of the arm member of FIG. 2, in a cross-section.
Figure 4:
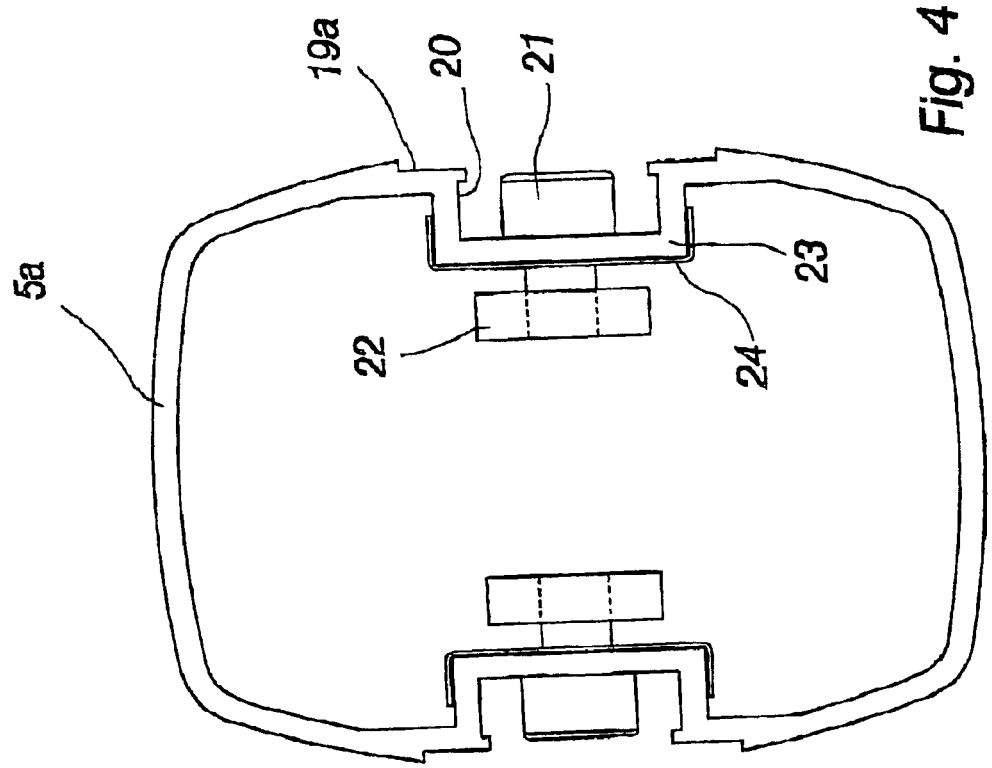
FIG. 4 shows a cross-section for an outer profile of the arm member of FIG. 2.
Figure 5:
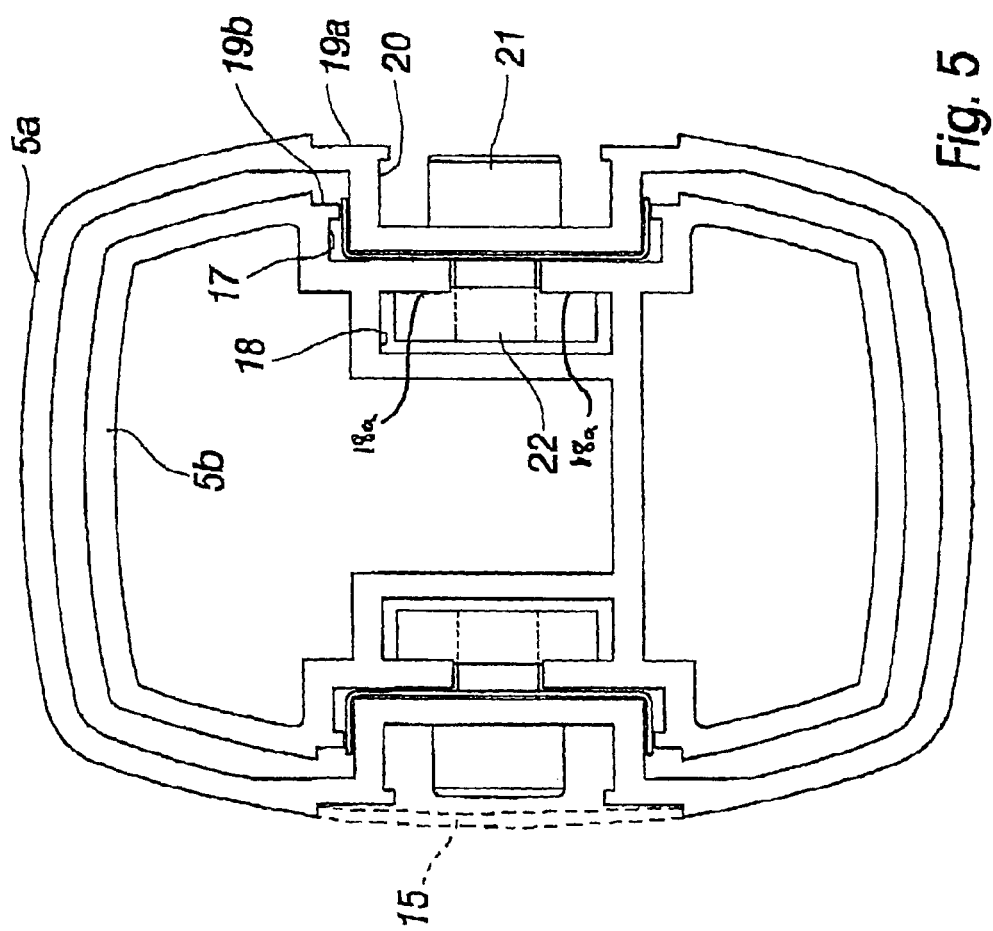
FIG. 5 shows a cross-section with the inner profile installed within the outer profile.
Figure 6:
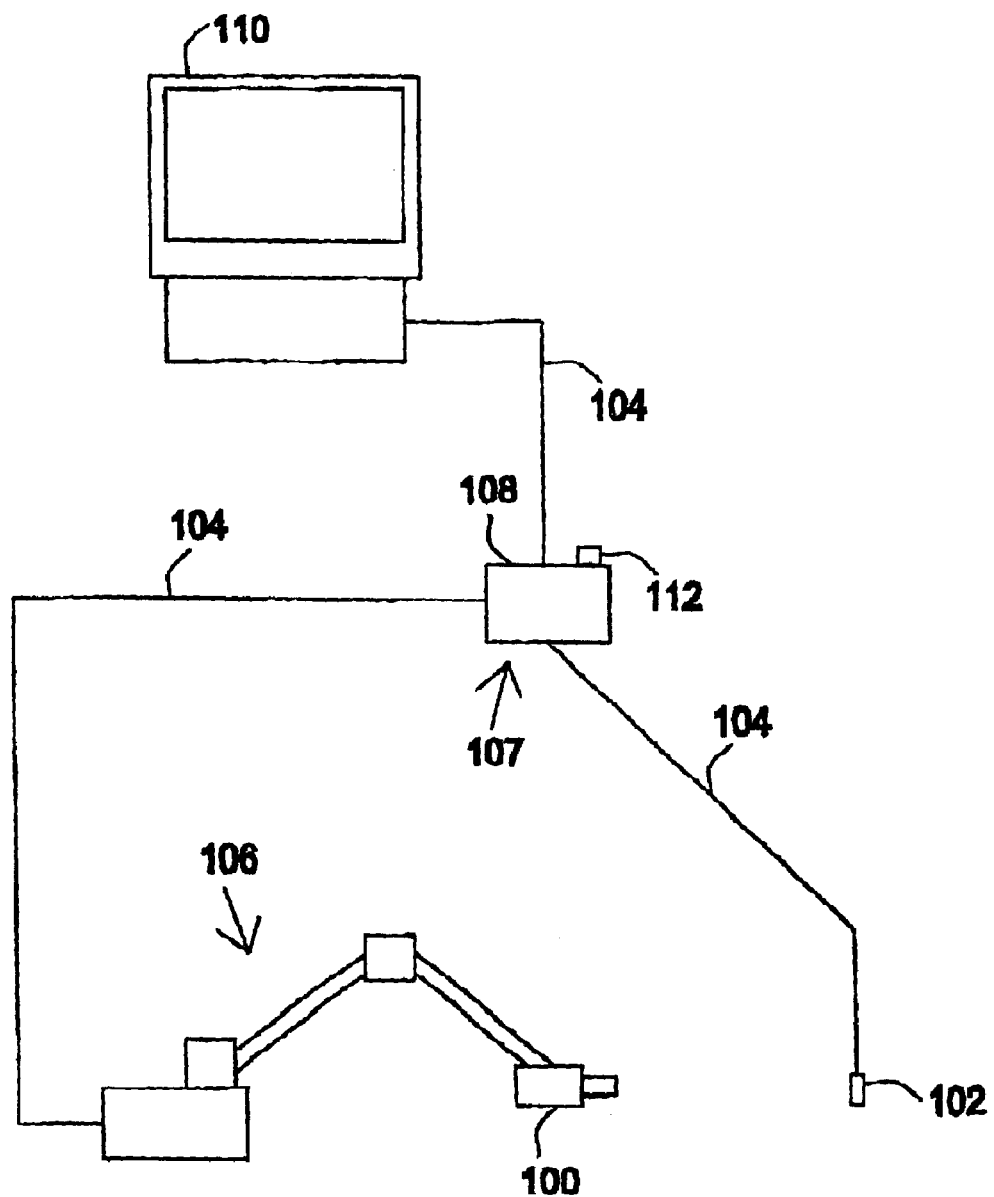
FIG. 6 shows in a schematic view an imaging arrangement of the prior art for intraoral imaging.

In reference to FIGS. 1–5, an X-ray apparatus 1 of the invention for intraoral imaging applications includes a first arm member 5, mounted on a support structure 4 and pivotable about a vertical axle 10 in a substantially horizontal plane, which comprises two telescopically fitted arm sections 5a, 5b. It has been proposed that the distal end of the arm 5 be provided with an arm member 6, adapted to be pivotable around a substantially vertical pivoting axle at an articulation 9 and having its opposite distal end fitted by means of a link element 8 with a third arm member 7, pivotable relative to the link element 8 around a substantially horizontal axis. To the distal end of the arm 7 is connected, by way of an articulated joint 11, an X-ray source 3 which is rotatable to various positions about a vertical axis in the articulated joint 11, as well as around a horizontal axle 12. The X-ray source 3 includes further a tube element 13 for emitting radiation in a desired direction.

The support structure 4 can be mounted on a wall or a separate base, and it may preferably house control electronics needed for the linkage 2.

According to FIGS. 2–5, the first arm member 5 comprises two telescopically fitted, substantially rectangular profiles 5a, 5b. The inner profile 5b has its two opposite outside surfaces formed with recesses 17 lengthwise of the profile, provided on the bottom thereof with longitudinal T-slots 18 including internal fastening surfaces 18a. The outer profile 5a has its inside surface formed with protrusions 23 complementary to said recesses 17 and provided with fastening holes for the passage of fastening elements 21, 22 from the outer profile's, outside surface to the. T-slot 18 for locking said profiles 5a, 5b in a desired relative position in the longitudinal direction thereof. The fastening elements 21, 22 are preferably located in the vicinity of the outer profile's 5a distal end on its two opposite sides. The fastening element 22 is preferably an elongated, cross-sectionally rectangular shaft, extending over a section of the outer profile's 5a length. The shaft 22 is preferably provided with threaded holes for securing the same, for example with two Allen screws 21, in its position against the fastening surface 18a of the inner profile's T-slot 18 for locking the profiles 5a and 5b in a desired relative lengthwise position.

The outer profile 5a has its outside surface formed with a lengthwise recess 20 complementary to that in the inner profile's outside surface. Adjacent to the recesses 17 and 20 are provided shoulders 19b and respectively 19a, on top of which can be installed a cover element 16 and respectively 15 for making the inner and outer outside surface essentially flat and for concealing the fastening elements 21. In terms of its material, the cover element 15 may comprise for example rubber or plastics, while a preferred material for the profiles 5a and 5b is aluminium. Reference numeral 24 represents a U-shaped spacer element, which is set in line with the fastening elements to fill a gap between the profile members in order to avoid distortion of the profile members 5a, 5b as the fastening elements are tightened.

The present inventive solution enables a relatively simple adjustability for a linkage, thus avoiding a necessity of manufacturing horizontal arms 5 in multiple sizes and, in addition, the design or dimensioning can be altered even afterwards with a comparatively simple procedure.

What is claimed is:

1. An X-ray apparatus for intraoral imaging applications, said apparatus comprising a linkage mounted on a support structure, to which is connected an X-ray source for generating X-radiation and directing the same to a receiver instrument placed in a patient's mouth, said linkage comprising:

a first arm member articulated to the support structure and adapted to be pivotable around a substantially vertical axis;

a second arm member connected to an end of the first arm member spaced from the support structure, said second arm member being adapted to be pivotable around a substantially vertical axis at a first end and around a horizontal axis at a second end; and a third arm member having an end connected to the second end of the second arm member and adapted to be pivotable around a substantially horizontal axis, an unconnected end of the third arm member having the X-ray source mounted thereon with an articulated joint which allows pivoting of the X-ray source to various positions, said first arm member designed to be adjustable in its length, wherein the first arm member comprises two telescopically fitted profiles of substantial rectangular cross section, an inner profile having its two opposite outside surfaces formed with recesses lengthwise of the inner profile and with a T-slot provided on a bottom side of each of the recesses, and an outer profile having its inside surface formed with inward protrusions complementary to said recesses and provided with fastening through-holes for the passage of fastening elements from the outer profile's outside surface to the T-slots for locking said profiles in a desired relative position in a longitudinal direction.

2. An apparatus as set forth in claim 1, wherein the outer profile has an outside surface provided with a lengthwise recess complementary to that present in an outside surface of the inner profile.

3. An apparatus as set forth in claim 2, wherein said recesses in the inner and outer profiles are provided with a cover element for making the inner and outer profiles' outside surfaces essentially flat.

4. An arm member of an x-ray apparatus, the arm member comprising:

a. an inner profile of substantially rectangular cross section, wherein the inner profile includes a recess formed in a lengthwise direction along each of a set of opposite sides of the inner profile;

b. an outer profile of substantially rectangular cross section telescopically fitted to the inner profile, wherein inside surfaces of the outer profile are formed with inward protrusions corresponding to each of the recesses of the inner profile;

c. a set of fastening elements configured to extend through a set of fastening holes in an outer surface of the outer profile; and d. a set of T-slots configured on bottom sides of the recesses of the inner profile, the set of T-slots configured to receive the set of fastening elements, thus locking the inner profile and the outer profile in a desired position, wherein the arm member is configured to couple an x-ray apparatus linkage to an x-ray source.

* * * * *